(12) United States Patent
Urban et al.

(10) Patent No.: US 12,316,047 B2
(45) Date of Patent: May 27, 2025

(54) STRAIN RELIEF FACILITY, CONNECTION ARRANGEMENT AND MEDICAL FACILITY

(71) Applicant: Siemens Healthcare GmbH, Erlangen (DE)

(72) Inventors: Andreas Urban, Bayern (DE); Volker Model, Fuerth (DE); Walter Kuchler, Nuremberg (DE); Ralph Trommer, Erlangen (DE); Ludwig Welker, Eggolsheim (DE); Josef Singer, Ingolstadt (DE)

(73) Assignee: Siemens Healthineers AG, Forchheim (DE)

( * ) Notice: Subject to any disclaimer, the term of this patent is extended or adjusted under 35 U.S.C. 154(b) by 422 days.

(21) Appl. No.: 17/846,563

(22) Filed: Jun. 22, 2022

(65) Prior Publication Data

US 2022/0416473 A1 Dec. 29, 2022

(30) Foreign Application Priority Data

Jun. 25, 2021 (DE) ...................... 20 2021 103 424.6

(51) Int. Cl.
*H01R 13/58* (2006.01)
*A61B 6/00* (2006.01)

(52) U.S. Cl.
CPC .............. *H01R 13/582* (2013.01); *A61B 6/56* (2013.01); *H01R 2201/20* (2013.01)

(58) Field of Classification Search
CPC ...... H01R 13/582; H01R 2201/20; A61B 6/56
See application file for complete search history.

(56) References Cited

U.S. PATENT DOCUMENTS

| | | | | |
|---|---|---|---|---|
| 3,711,633 A | * | 1/1973 | Ghirardi | H02G 15/18 285/133.11 |
| 4,838,808 A | * | 6/1989 | Fujiura | H01R 13/6275 439/372 |
| 5,315,062 A | * | 5/1994 | Hoshino | H01R 13/506 439/658 |
| 5,643,693 A | * | 7/1997 | Hill | H01M 50/296 429/123 |
| 5,688,144 A | * | 11/1997 | Kosuge | H01R 13/516 439/466 |
| 6,059,602 A | * | 5/2000 | Ward | H01R 13/6581 439/465 |
| 6,203,362 B1 | * | 3/2001 | Tsuji | H01R 13/506 439/470 |
| 6,540,547 B2 | * | 4/2003 | Zweigle | H01R 13/5804 439/468 |

(Continued)

FOREIGN PATENT DOCUMENTS

DE 102014206295 A1 10/2015
EP 3217185 A1 9/2017

*Primary Examiner* — Thanh Tam T Le
(74) *Attorney, Agent, or Firm* — Harness, Dickey & Pierce, P.L.C.

(57) ABSTRACT

A strain relief facility for a coaxial cable that is connectable to an electronics unit via an associated plug, includes two half-shells forming a receiver for the coaxial cable and the associated plug, and a fastening facility to fasten the strain relief facility to the electronics unit, and to fasten the half-shells to one another. The receiver has at least one cable section to receive the coaxial cable and a plug section to receive the plug.

25 Claims, 3 Drawing Sheets

(56) References Cited

U.S. PATENT DOCUMENTS

| | | | | |
|---|---|---|---|---|
| 8,523,602 | B2* | 9/2013 | Figie | H01R 13/6581 |
| | | | | 439/466 |
| 8,568,159 | B2* | 10/2013 | Noda | H01R 13/562 |
| | | | | 439/470 |
| 8,939,788 | B2* | 1/2015 | Eminovic | H01R 43/26 |
| | | | | 439/465 |
| 9,608,361 | B2* | 3/2017 | Vaccaro | H01R 13/5205 |
| 10,249,976 | B1* | 4/2019 | Thomas | H01R 13/562 |
| 10,530,136 | B2* | 1/2020 | Terashima | H02G 3/0462 |
| 10,665,980 | B2* | 5/2020 | Saitoh | H02G 3/0462 |
| 11,942,768 | B2* | 3/2024 | Yamamoto | H02G 3/06 |
| 2017/0261575 | A1 | 9/2017 | Model | |
| 2020/0222022 | A1 | 7/2020 | Model | |

* cited by examiner

STRAIN RELIEF FACILITY, CONNECTION ARRANGEMENT AND MEDICAL FACILITY

CROSS-REFERENCE TO RELATED APPLICATION(S)

The present application claims priority under 35 U.S.C. § 119 to German Patent Application No. 20 2021 103 424.6, filed Jun. 25, 2021, the entire contents of which are incorporated herein by reference.

FIELD

Embodiments of the present invention relate to a strain relief facility for a coaxial cable, in particular a coaxial cable subject to a movement, and an associated plug, wherein the coaxial cable can be connected to an electronics unit via the plug. In addition, embodiments of the present invention relate to a connection arrangement with such a strain relief facility and a medical facility.

BACKGROUND

To transfer data or signals via a radio-frequency carrier signal it is already known in the prior art for use to be made of coaxial cables, which have an inner conductor and an outer conductor (also called a sheathed conductor or shield wire). The inner conductor runs coaxially to the outer conductor within the same. Such coaxial cables have excellent shielding and immunity to interference. Connection arrangements with coaxial cables can for example connect different electronics units to one another, for example a radio-frequency transmission unit and a radio-frequency receiving unit. In this case plugs are normally employed to connect the coaxial cable to a respective electronics unit. Problems can arise especially if for example two opposably moving electronics units are to be connected via radio-frequency technology, or else if mechanical robustness is required due to a movement of at least one electronics unit which would also affect the coaxial cable. Problems such as these occur in particular in the case of medical facilities, in other words medical engineering facilities, wherein for example in a computed tomography facility a recording arrangement with an X-ray detector and an X-ray generator is to be moved quickly around a patient. In this case information is to be transmitted from the X-ray detector to an evaluation facility, which normally does not move.

In this connection a device is described in DE 10 2014 206 295 A1 for the contact-free transmission of electrical signals in a computed tomography system, which instead of sliding contacts or the like uses slit coaxial coupling elements arranged with a gap between them.

Other areas of application, in which relative movements between radio-frequency transmission units and/or receiving units or electronics units in general may occur include moving patient examination tables, into which for example an X-ray detector and/or in the case of magnetic resonance imaging a local coil may be integrated.

To cope with forces occurring because of the movement, for example centrifugal forces, it has been proposed to use conventional, screw-fixed 2.92 mm plugs (K-type plugs) as plugs for the connection to an electronics unit, for example in the frequency range between 17 and 30 GHz. However, plugs such as these are expensive and require a special tool for assembly, since a particular torque is needed if they are to work reliably. Another problem with these 2.92 mm plugs is that they have very limited shielding properties as regards electromagnetic emissions (EME) and also as regards electromagnetic interference immunity (EMI). However, in particular in the area of use of medical imaging, in other words for medical facilities such as computed tomography facilities and/or magnetic resonance facilities, strict requirements prevail as regards both electromagnetic emissions (normally in the frequency range of the data transmission system attributable to sheath waves) and also in respect of electromagnetic interference immunity (for example because of the use of larger electric motors and/or the operation of measurement equipment such as for example X-ray tubes, measurement coils or the like). In this case it may also be noted that a simple microwave plug connector is not possible, since this cannot absorb the mechanical forces, in particular in a rotating system such as a computed tomography facility.

SUMMARY

Embodiments of the present invention specify an option for connecting a coaxial cable to an electronics unit, said option being inexpensive, capable of being implemented without special tools, mechanically robust and satisfying requirements as regards EME and EMI.

Embodiments of the present invention provide a strain relief facility, a connection arrangement and a medical facility.

In particular therefore a strain relief facility of the type mentioned in the introduction is provided, which inventively has two half-shells forming a receiver for the cable and the plug and a fastening facility for fastening the strain relief facility to the electronics unit, and the half-shells to one another, wherein the receiver has at least one first section for receiving the coaxial cable and a second section for receiving the plug.

In accordance with embodiments of the present invention it is therefore proposed to use a strain relief which initially enables other plug variants that can be used without special tools and/or screw fastening to be employed instead of the 2.92 mm plug that is typically employed. In this case the particular preference is to use an SMP plug (SMP—"Sub Miniature Push-on"), in particular as part of an SMP connector to be snapped into place. Such connectors include a latching mechanism, which can also be referred to as a snap-in mechanism, such that a secure connection can be established without special tools, as a result of which such SMP plugs are better suited for possible service operations. The use of a plug that can be used without special tools and without screw assembly, in particular a snap-in SMP plug, simplifies the establishment and also the maintenance of the resultant connection arrangement. Yet such plugs, in particular SMP plugs, are mostly designed such that an axial and/or radial alignment tolerance is present.

A misalignment of the plugs is therefore tolerated in the context of the SMP plug-in connection, but impairs the transmission behavior in the transmission frequency range, in particular between 17 and 30 GHz. Thus in particular, use in a rotating environment, such as for example in the case of a computed tomography facility, is made difficult.

Consequently, embodiments of the present invention proposes a specially configured strain relief facility, which besides its basic strain relief function additionally facilitates the guidance of the SMP plug, in that a corresponding plug section of the receiver is provided which ensures a correct alignment of the plug for the connection of the electronics unit, in particular because a corresponding fastening can be made to the electronics unit, adjacent to the connector. Thanks to the at least one cable section the desired alignment of the coaxial cable to the plug is also created, so that despite the tolerances an excellent quality of transmission and connection is achieved. Moreover, the two-part embodiment of the receiver further supports the plug in particular against forces acting to disconnect it, since normally the at least one cable section will be dimensioned to be narrower than the plug section.

In a particularly advantageous embodiment of the present invention it can however additionally be provided that the half-shells consist of an electrically conductive material, in particular a metal, and the receiver has a first cable section for receiving the insulated coaxial cable and a second, in particular central, cable section for receiving the stripped coaxial cable, such that an outer conductor of the coaxial cable contacts the conductive material. Thus not only are mechanical stability and correct alignment supported, but also adherence to requirements regarding electromagnetic emissions and electromagnetic interference immunity (EME and EMI). To this end it is proposed to configure the receiver of the strain relief in three regions. Initially the substantially cylindrical first cable section, known in principle, for receiving the complete coaxial cable having its insulation is provided for. This then transitions into a central, second cable section, which is likewise cylindrical, but is designed to be narrower than the first section, and consequently with a smaller radius. In this second cable section the coaxial cable is to be stripped prior to being placed into the receiver, such that the outer conductor (often also referred to as a shield wire or sheathed conductor) is exposed. In the receiver this outer conductor is then surrounded in a form-fit manner by the corresponding portions of the half-shells, which are designed to be electrically conductive. In this way a shielding from sheath waves in the transmission frequency range, in particular 17-30 GHz, can be provided, because the strain relief facility, specifically at least one of the half-shells, further preferably has at least one contact surface for the electrically conductive contacting of an electrically conductive housing of the electronics unit.

Because such electrically conductive housings of electronics units are normally grounded, a connection of the outer conductor to ground is established, wherein it can particularly advantageously be provided that the half-shells are designed as a shield for sheath waves in the transmission frequency range, in particular in a frequency range between 17 and 30 GHz.

Finally, in the third area, the plug section of the receiver, the plug, in particular SMP plug, is itself received, such that thanks to the way it is guided the correct adjustment of the connection is facilitated, in particular ensured. To further facilitate the correct relative alignment of coaxial cable and plug as well as the alignment thereof, the at least one cable section, in particular therefore the first and the second cable section, of the receiver can form an axially symmetrical cable run to the plug. In summary, the strain relief facility can particularly advantageously therefore achieve the following properties besides the absorption of mechanical forces:

Axially symmetrical cable run to the plug,
Shielding for sheath waves in the frequency range of the transmission signal, in particular 17-30 GHz, and
Short-circuit of the outer conductor to ground, in particular at least in the frequency range 0 Hz-1 GHz.

In this way, in addition to the strain relief typical for strain relief facilities, an excellent guidance directly in the connection region to the electronics unit is provided, the misalignments are at least substantially prevented, and in addition improved insulation in respect of electromagnetic emissions and electromagnetic interference immunity is provided, wherein in particular the strain relief facility forms a sheath wave barrier (which can also be referred to as a sheath wave filter) which ultimately prevents unwanted sheath waves from reaching the electronics unit or from having emissive interference effects.

Overall the solution described is not only appreciably more inexpensive, but also easier to manage, since in particular when the plug is configured as an SMP plug no special tool is required. Thanks to the structure described the strain relief facility can be employed in the demanding setting with heightened mechanical stresses, e.g. in a rotating environment, wherein moreover the robustness as regards electromagnetic emissions and electromagnetic interference immunity is appreciably increased.

In a particularly expedient development of the inventive strain relief facility it can be provided that the fastening facility has a first fastener (or, alternatively, first fastening device or first fastening means) for fastening at least one of the half-shells to the electronics unit and a second fastener (or, alternatively, second fastening device or second fastening means), separate therefrom, for fastening the half-shells to one another. In this way it is in particular possible initially to fasten the one half-shell adjacent to the connector of the electronics unit thereto, such that the receiver, still open on one side, is aligned to the connector. Then, after a corresponding stripped insulation, the coaxial cable with the plug can be inserted into the receiver and the plug-in connection can be established. Finally the receiver is closed by the second half-shell and both the half-shells are fastened to one another using the second fastener, such that the cable and the plug are held in the receiver in a form-fit manner, in particular subject to at least slight compression. In a concrete embodiment it can be provided that the first fastener has screws with associated feed-through openings or recesses at least in a lower one of the half-shells and the second fastener has screws with associated screw receivers in the half-shells. It is especially advantageous, in particular in respect of the manufacture, if both half-shells are designed identically, wherein a section having the feed-through openings or recesses of the first fastener is then preferably designed to be not as high as the rest of the half-shells, in order to create a receiving space for the screw head.

In this embodiment it is consequently possible initially to screw one of the half-shells onto the electronics unit, whereupon the receiver can be closed by a further, simple screw connection and the strain relief facility can be taken into operation.

In the context of embodiments of the present invention it is further advantageous if the edges of the entry opening for the coaxial cable into the strain relief facility are rounded off in the region of the entry opening to facilitate bending radii of the coaxial cables. This means that the edges are rounded off into the first section, in order to ensure minimum bending radii of the coaxial cable. In this way the coaxial cable is not only protected against damage by edges that are not excessively sharp, but can also adopt larger bending radii, further contributing to the protection of the cable, in particular in the given movement situation.

A metal, in particular aluminum, can particularly advantageously be used as the material for the half-shells. The half-shells can for example be manufactured by die casting.

Besides the strain relief facility, embodiments of the present invention also relate to a connection arrangement, comprising a coaxial cable with a plug and a strain relief facility in accordance with embodiments of the present invention. All explanations regarding the inventive strain relief facility can be transposed analogously to the inventive connection arrangement, with which consequently the aforementioned advantages can likewise be obtained.

In this case the plug can, as has already been stated, particularly advantageously be an SMP plug, in particular a snap-in SMP plug.

However, embodiments of the present invention also allow a more flexible choice in respect of the coaxial cable. Thus it is for example conceivable also to use what is known as a semi-flexible coaxial cable, instead of an ultra-flexible coaxial cable frequently used to date. Such semi-flexible coaxial cables are also referred to as "hand-formable coaxial cables", "semi-flex cables" or "conformable semi-rigid lines". In this case for example the outer conductor can be formed by an outer conductor fabric completely impregnated with zinc. Although such coaxial cables make higher demands as regards manageability, they have appreciably improved properties as regards the shielding properties while at the same time costing relatively little, such that they also prove to be particularly advantageous in the context of embodiments of the present invention.

Finally embodiments of the present invention also relate to a medical facility, having at least two opposably movable components, each with at least one electronics unit, wherein to connect electronics units of the components at least one connection arrangement in accordance with embodiments of the present invention is provided. The explanations in respect of the strain relief facility and the connection arrangement also continue to apply in respect of the medical facility.

In particular the medical facility can be a computed tomography facility, wherein the connection arrangement for example can be provided on the part of a rotatably moving electronics unit of the receiver arrangement, in particular an X-ray detector. If nevertheless only one plug-in SMP connection is used, the connector withstands the mechanical strains thanks to the use of the strain relief facility, enables an alignment for excellent transmission quality, also in particular provides excellent shielding and represents an inexpensive and easily maintainable solution.

In this case the connection arrangement can in one development comprise at least one contact-free data transmission device. There can for example be an embodiment in a computed tomography facility as is described in DE 10 2014 206 295 A1 already cited in the introduction.

BRIEF DESCRIPTION OF THE DRAWINGS

Further advantages and details of the present invention emerge from the exemplary embodiments described below and on the basis of the drawings, in which.

DETAILED DESCRIPTION

Figure 1:
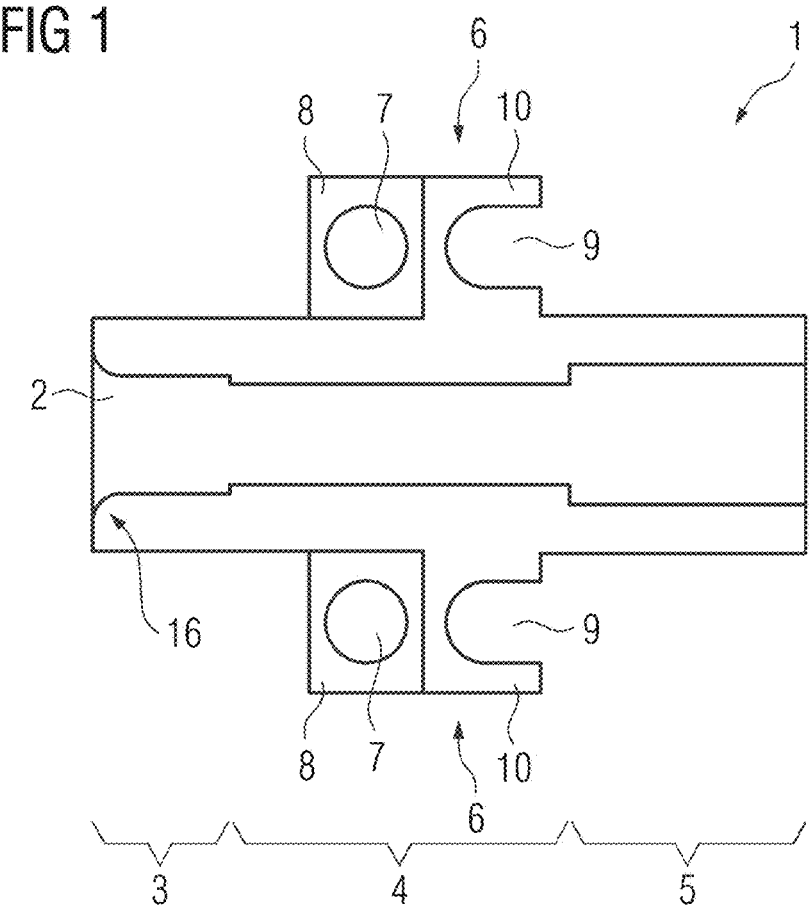
FIG. 1 shows a plan view of a lower half-shell of an inventive strain relief facility according to embodiments of the present invention.

FIG. 1 shows a plan view of a half-shell 1 of an inventive strain relief facility, which in the present case comprises two identically configured, die-cast half-shells 1 of this type consisting of aluminum. The half-shell 1 can be seen to have a central, at least substantially semicircular depression 2, which, if the two half-shells 1 are laid together with the sides having the depression 2, form a receiver for a coaxial cable with plug. The depression 2 or this receiver can be seen to have three sections 3, 4, 5, which are distinguished in particular by being different sizes. A first cable section 3 and a second cable section 4 serve to receive the coaxial cable, while an overall third plug section 5 serves to receive the plug already provided on the coaxial cables, here a snap-in SMP plug. In this case the coaxial cable in the first cable section 3 is still provided with its outer insulation, while in the second cable section 4 it is stripped, such that the outer conductor is exposed.

Laterally the half-shell 1 has projecting portions forming a fastening facility 6, which in the present case has a feed-through opening 7 for first fastener 8 to fasten the half-shell 1 to an electronics unit, to which the coaxial cable is to be connected via the plug, in a lower portion and a recess 9 for second fastener 10, which serve to fasten both the half-shells 1 to one another. The first fastener 8 and the second fastener 10 each of course have associated screws (not shown in FIG. 1). Thanks to the lowered design in the portion of the first fastener 8 space is created for the screw head—despite the identical design of both half-shells 1.

Figure 2:
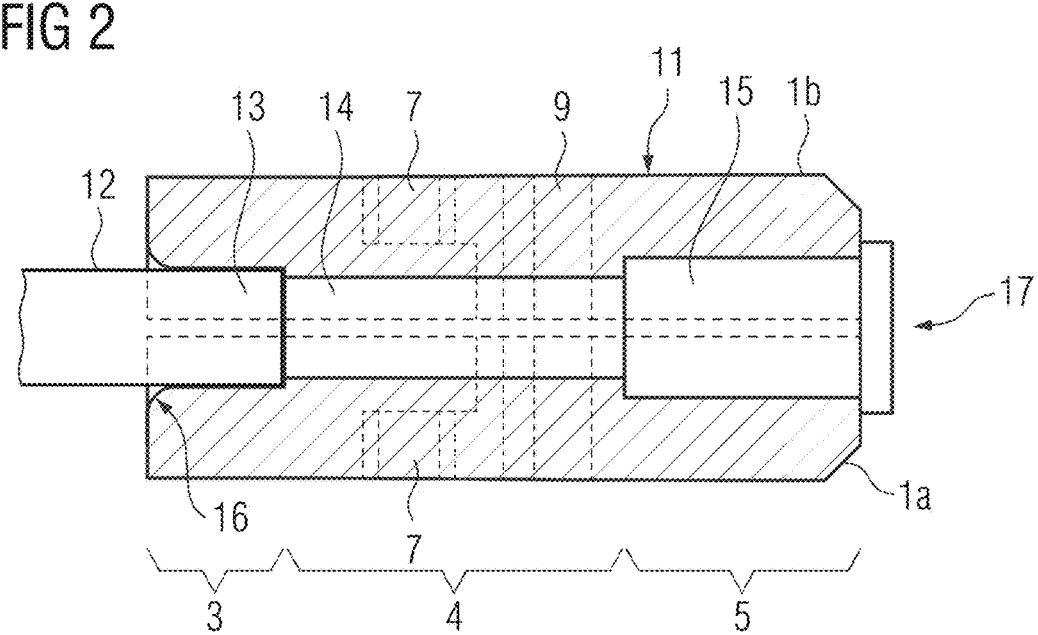
FIG. 2 shows a cross-section through an inventive strain relief facility according to embodiments of the present invention.

FIG. 2 shows the strain relief facility 11 assembled from the lower half-shell 1a and the upper half-shell 1b in a schematic cross-section. It can be seen that the coaxial cable 12, which is a semi-flexible coaxial cable, lies, with a first portion 13 that still has the insulation, in the first cable section 3, and with a stripped portion, consequently the bare outer conductor 14, in the second cable section 4, to which the snap-in SMP plug 15 is connected in the plug section 5.

As can be seen from FIG. 1 and FIG. 2, the edges 16 are designed as rounded off in the region of the entry opening of the first cable section 3.

Together with the coaxial cable 12 with plug 15 the strain relief facility 11 forms an inventive connection arrangement 17.

Figure 3:
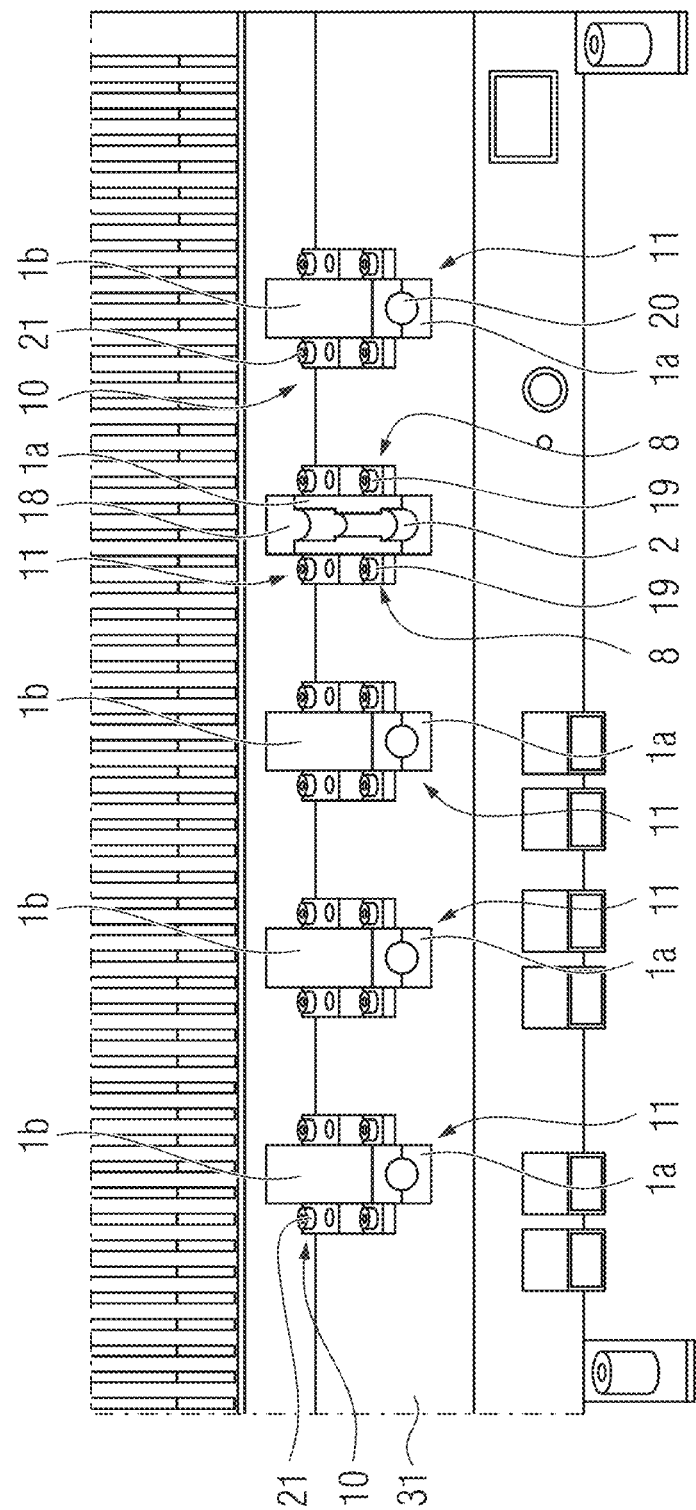
FIG. 3 shows a perspective view of an electronics unit with strain relief facilities mounted thereon, according to embodiments of the present invention.

FIG. 3 shows multiple strain relief facilities 11 upstream of corresponding connectors 18 of an electronics unit 19 mounted thereon, wherein in the case of one of these strain relief facilities 11 the upper half-shell 1b has been omitted for clarity. It can be seen that for use the lower half-shell 1a is initially fastened to the electronics unit 31 via screws 19 of the first fastener 8, such that the depression 2 is aligned as precisely as possible to the connector 18. In the case of the strain relief facility 11 shown in full, the receiver 20 formed by both the half-shells 1a, 1b can also be clearly identified.

In the state of the strain relief facility 11 still shown as open the coaxial cable 12 with the plug 15 can now be placed into the depression 2 of the lower half-shell 1a accurately, consequently in a form-fit manner, whereupon the second half-shell 1b can be fastened via screws 21 of the second fastener 10, such that the coaxial cable 12 and the plug 15 are fixed in the receiver 20.

It can be seen that at least the lower half-shell 1a is electrically conductively connected by the screws 19 and by corresponding contact surfaces to the metal housing, in other words also the electrically conductive housing, of the electronics unit 31, wherein this housing is connected to ground. Because at the same time in the second cable section 4 the outer conductor 14 contacts the half-shells 1a, 1b, the strain relief facility 11 has a shielding effect in the region of the plug 15 and also acts as a sheath wave barrier in the range of the transmission frequencies, here for example 17-30 GHz.

Figure 4:
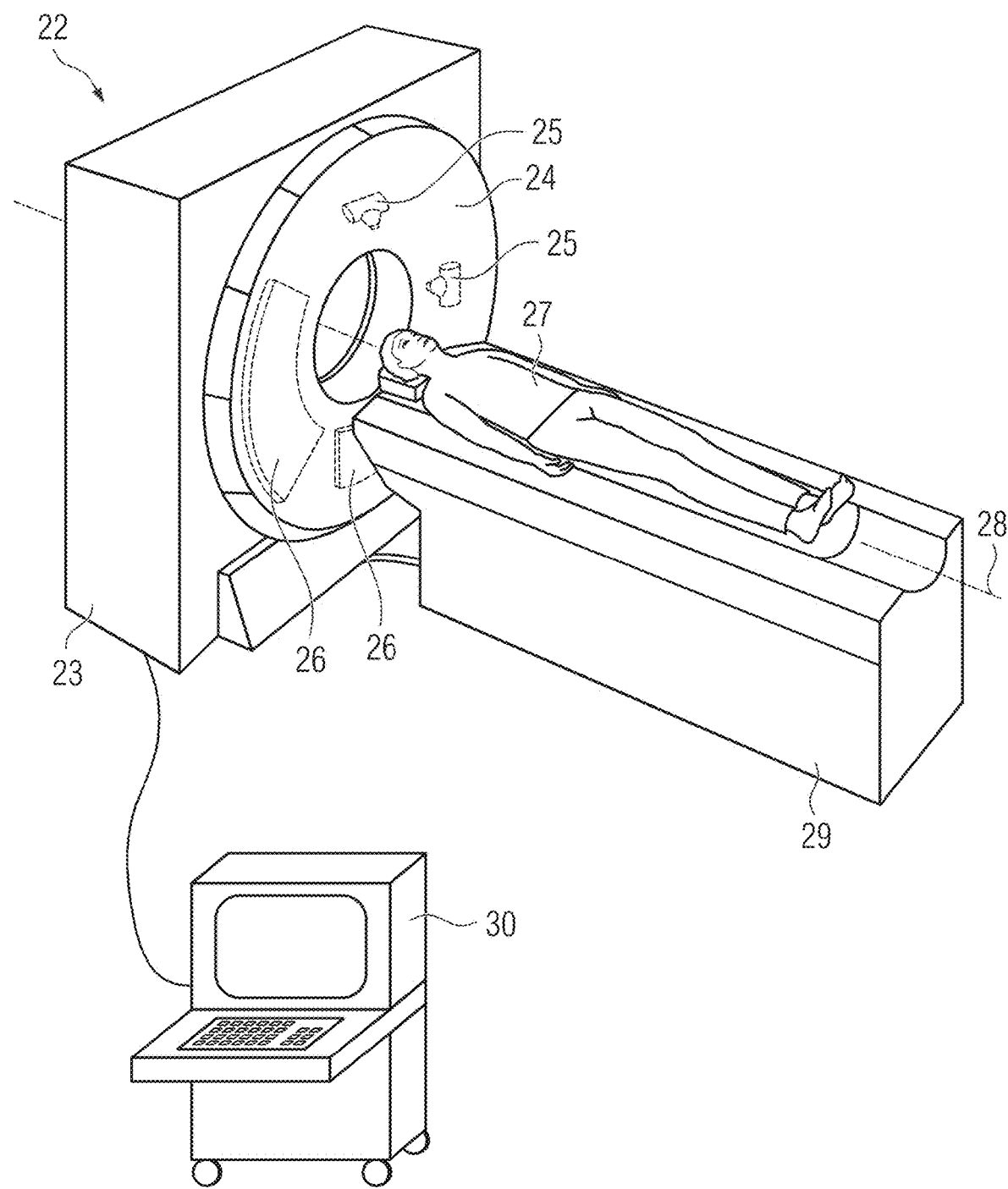
FIG. 4 shows a schematic diagram of a computed tomography facility according to embodiments of the present invention.

FIG. 4 shows as an example of a medical facility 23 in which the connection arrangement 17 can be employed, for example in respect of the rotating X-ray detector and/or the rotating X-ray tube, a computed tomography facility, which, as is known in principle, has a gantry 23, inside which is a rotatable portion 24, on which two receiver arrangements are each arranged with X-ray generator 25 and X-ray detectors 26. For the examination, a patient 27 is moved into a scanning region with the help of a patient couch of a patient examination table 29 that can be displaced along a central axis 28, such that projection images can be scanned from different projection angles.

The medical facility 22 is controlled by a control facility 30. A reconstruction of a three-dimensional image dataset from two-dimensional projection images can for example take place there.

In particular in the case of the transmission of the X-ray data by the X-ray detectors 26 from the rotatable portion 24 it is necessary to transmit a large quantity of data despite the movement, for which reason data transmission takes place via coaxial cables at a carrier frequency between 17 and 30 GHz and a contact-free transmission device is used, as is described for example in DE 10 2014 206 295 A1. The inventive strain relief facility 11 is employed for the connection to electronics units associated with the X-ray detector 26.

Other areas of application are however also conceivable, for example on the moving portion of the patient examination table 29.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of the embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing embodiments. The present invention may, however, be embodied in many alternate forms and should not be construed as limited to only the embodiments set forth herein.

Although the present invention has been illustrated and described in greater detail by the preferred exemplary embodiment, the present invention is not restricted by the disclosed examples and other variations can be derived therefrom by the person skilled in the art, without departing from the scope of protection of the present invention.

What is claimed is:

1. A strain relief device for a coaxial cable that is connectable to an electronics unit via an associated plug, the strain relief device comprising:
    two half-shells forming a receiver for the coaxial cable and the associated plug, the receiver having at least one cable section configured to receive the coaxial cable and a plug section configured to receive the associated plug; and
    a fastening device configured to
        fasten the strain relief device to the electronics unit, and
        fasten the two half-shells to one another,
        the fastening device including a first fastener configured to fasten at least one of the two half-shells to the electronics unit, a first feed-through opening of the first fastener being aligned perpendicular to a plug direction of the associated plug.

2. The strain relief device as claimed in claim 1, wherein the two half-shells include an electrically conductive material; and
    the at least one cable section includes
        a first cable section configured to receive an insulated portion of the coaxial cable, and
        a second cable section configured to receive a stripped portion of the coaxial cable, such that an outer conductor of the coaxial cable contacts the electrically conductive material.

3. The strain relief device as claimed in claim 2, further comprising:
    at least one contact surface configured to electrically and conductively contact an electrically conductive housing of the electronics unit.

4. The strain relief device as claimed in claim 2, wherein the two half-shells are configured as a sheath wave barrier in at least one transmission frequency range.

5. The strain relief device as claimed in claim 2, wherein the first cable section and the second cable section form an axially symmetrical cable run to the associated plug.

6. The strain relief device as claimed in claim 1, wherein the fastening device comprises:
    a second fastener configured to fasten the two half-shells to one another, the second fastener being separate from the first fastener.

7. The strain relief device as claimed in claim 6, wherein the first fastener has screws with associated feed-through openings or recesses in at least a lower one of the two half-shells, the associated feed-through openings of recesses including the first feed-through opening; and
    the second fastener has screws with associated screw receivers in the two half-shells.

8. The strain relief device as claimed in claim 1, wherein edges of an entry opening for the coaxial cable into the strain relief device are rounded off in a region of the entry opening to facilitate a bending radii of the coaxial cable.

9. A connection arrangement comprising a coaxial cable with an associated plug and the strain relief device as claimed in claim 1.

10. The connection arrangement as claimed in claim 9, wherein the associated plug is an SMP plug.

11. The connection arrangement as claimed in claim 9, wherein the coaxial cable is semi-flexible.

12. A medical device having at least two opposably movable components, each of the at least two opposably movable components having at least one electronics unit, and the medical device comprising:
    at least one connection arrangement as claimed in claim 9, the at least one connection arrangement configured to connect the at least one electronics unit in each of the at least two opposably movable components to one another.

13. The medical device as claimed in claim 12, wherein the at least one connection arrangement comprises at least one contact-free data transmission device.

14. The medical device as claimed in claim 12, wherein the medical device is a computed tomography device.

15. The strain relief device of claim 1, wherein the coaxial cable is a moveable coaxial cable.

16. The strain relief device of claim 2, wherein the electrically conductive material is a metal.

17. The strain relief device of claim 2, wherein the second cable section is a central cable section.

18. The strain relief device of claim 4, wherein the at least one transmission frequency range includes a frequency range between 17 and 30 GHz.

19. The connection arrangement of claim 10, wherein the SMP plug is a snap-in SMP plug.

20. The strain relief device as claimed in claim 3, wherein the two half-shells are configured as a sheath wave barrier in at least one transmission frequency range.

21. The strain relief device as claimed in claim 3, wherein the first cable section and the second cable section form an axially symmetrical cable run to the associated plug.

22. The strain relief device as claimed in claim 4, wherein the first cable section and the second cable section form an axially symmetrical cable run to the associated plug.

23. The strain relief device as claimed in claim 2, wherein the fastening device comprises:
    a second fastener configured to fasten the two half-shells to one another, the second fastener being separate from the first fastener.

24. The strain relief device as claimed in claim 4, wherein the fastening device comprises:
    a second fastener configured to fasten the two half-shells to one another, the second fastener being separate from the first fastener.

25. The strain relief device as claimed in claim 3, wherein the fastening device comprises:
   a second fastener configured to fasten the two half-shells to one another, the second fastener being separate from the first fastener.

* * * * *